US007265093B2

(12) United States Patent
Khosla et al.

(10) Patent No.: US 7,265,093 B2
(45) Date of Patent: Sep. 4, 2007

(54) DRUG THERAPY FOR CELIAC SPRUE

(75) Inventors: Chaitan Khosla, Palo Alto, CA (US); Kihang Choi, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 456 days.

(21) Appl. No.: 10/716,846

(22) Filed: Nov. 18, 2003

(65) Prior Publication Data

US 2004/0167069 A1    Aug. 26, 2004

Related U.S. Application Data

(63) Continuation-in-part of application No. PCT/US03/15343, filed on May 14, 2003.

(60) Provisional application No. 60/428,033, filed on Nov. 20, 2002, provisional application No. 60/422,933, filed on Oct. 31, 2002, provisional application No. 60/392,782, filed on Jun. 28, 2002, provisional application No. 60/380,761, filed on May 14, 2002.

(51) Int. Cl.
*A61K 38/00* (2006.01)

(52) U.S. Cl. .................... 514/16; 424/1.59; 530/326; 530/327; 530/328

(58) Field of Classification Search .................. 514/16
See application file for complete search history.

(56) References Cited

U.S. PATENT DOCUMENTS

| | | | | |
|---|---|---|---|---|
| 4,912,120 | A | * | 3/1990 | Castelhano et al. ......... 514/380 |
| 4,929,630 | A | * | 5/1990 | Castelhano et al. ......... 514/380 |
| 5,834,428 | A | | 11/1998 | Drucker |
| 6,197,356 | B1 | | 3/2001 | Girsh |
| 6,319,726 | B1 | | 11/2001 | Schuppan et al. |
| 6,410,550 | B1 | | 6/2002 | Coe et al. |
| 2001/0036639 | A1 | | 11/2001 | Fine |
| 2002/0076834 | A1 | | 6/2002 | Detlef et al. |
| 2004/0241664 | A1 | | 12/2004 | Dekker et al. |

FOREIGN PATENT DOCUMENTS

EP    0 905 518 A1    3/1999

| WO | WO94/26774 | 11/1994 |
|---|---|---|
| WO | WO 01/25793 A2 | 4/2001 |
| WO | WO 03/068170 A2 | 8/2003 |

OTHER PUBLICATIONS

Piper et al. High selectivity of human tissue transglutaminase for immunoactive gliadin peptides: implications for celiac sprue. Bichemistry. Jan. 8, 2002;41(1):386-93.*
Ahnen et al., Intestinal Aminooligopeptidase in vivo Synthesis on Intracellualar Membranes of Rat Jejunum, J. Biol. Chem., (1982), 257: 12129-35.
Arentz-Hansen et al., The Intestinal T Cell Response to α-Gliadin in Adult Celiac Disease is Focused on a Single Deamidated Glutamine Targeted by Tissue Transglutaminase, J. Exp. Med., (2000), 191: 603-12.
Bordusa et al., The Specificity of Prolyl Endopeptidase From *Flavobacterium meningoseptum*: Mapping the S' Subsites by Positional Scanning via Acyl Transfer, Bioorg. Med. Chem., (1998), 6: 1775-80.
Lahteenoja et al., Local Challenge on Oral Mucosa With an α-Gliadin Related Synthetic Peptide in Patients With Celiac Disease, Am. J. Gastroenterol., (2000), 95: 2880.
Schuppan, Detlef, Special Reports and Reviews Current Concepts of Celiac Disease Pathogenesis. Gastroenterology, (2000), 119: 234-42.
Wieser, Herbert, The Precipitating Factor in Coeliac Disease, Baillieres Clin Gastroenterol, (1995) . 9(2):191-207.
Yoshimoto et al., Prolyl Endopeptidase From *Flavobacterium meningosepticum*: Cloning and Sequencing of the Enzyme Gene, J. Biochem., (1991), 110: 873-8.
Greenberg, C., et al., "Transglutaminases: multifunctional cross-linking enzymes that stabilize tissues," (1991) *FASEB J.*, 5:3071-3077.
Hitomi, K., et al., "GTP, an inhibitor of transglutaminases, is hydrolyzed by tissue-type transglutaminase (TGase 2) but not by epidermal-type transglutaminase (TGase 3)," (2000) *Biosci. Biotechnol. Biochem.*, 64(3):657-659.
Sardy, M., et al., "Epidermal transglutaminase (TGase 3) is the autoantigen of *Dermatitis herpetiformis*," (2002) *J. Exp. Med.*, 195(6):747-757.

* cited by examiner

*Primary Examiner*—Cecilia J. Tsang
*Assistant Examiner*—Maury Audet
(74) *Attorney, Agent, or Firm*—Bozicevic, Field & Francis LLP; Pamela J. Sherwood

(57) ABSTRACT

Administering an effective dose of a tTGase inhibitor to a Celiac or dermatitis herpetiformis patient reduces the toxic effects of toxic gluten oligopeptides, thereby attenuating or eliminating the damaging effects of gluten.

10 Claims, No Drawings

DRUG THERAPY FOR CELIAC SPRUE

CROSS-REFERENCE TO RELATED APPLICATIONS

This application is a continuation in part of International Application PCT/US03/15343, filed May 14, 2003; and claims priority to U.S. Provisional Application No. 60/380,761 filed May 14, 2002; to U.S. Provisional Application No. 60/392,782 filed Jun. 28, 2002; and to U.S. Provisional application No. 60/422,933, filed Oct. 31, 2002, and to U.S. Provisional Application No. 60/428,033, filed Nov. 20, 2002, each of which are herein specifically incorporated by reference.

This invention was made with Government support under contract 9910949 awarded by the National Science Foundation. The Government has certain rights in this invention.

BACKGROUND OF THE INVENTION

In 1953, it was first recognized that ingestion of gluten, a common dietary protein present in wheat, barley and rye causes a disease called Celiac Sprue in sensitive individuals. Gluten is a complex mixture of glutamine- and proline-rich glutenin and prolamine molecules and is thought to be responsible for induction of Celiac Sprue. Ingestion of such proteins by sensitive individuals produces flattening of the normally luxurious, rug-like, epithelial lining of the small intestine known to be responsible for efficient and extensive terminal digestion of peptides and other nutrients. Other clinical symptoms of Celiac Sprue include fatigue, chronic diarrhea, malabsorption of nutrients, weight loss, abdominal distension, anemia, as well as a substantially enhanced risk for the development of osteoporosis and intestinal malignancies such as lymphoma and carcinoma. The disease has an incidence of approximately 1 in 200 in European populations and is believed to be significantly under diagnosed in other populations.

A related disease is dermatitis herpetiformis, which is a chronic eruption of the skin characterized by clusters of intensely pruritic vesicles, papules, and urticaria-like lesions. IgA deposits occur in almost all normal-appearing and perilesional skin. Asymptomatic gluten-sensitive enteropathy is found in 75 to 90% of patients and in some of their relatives. Onset is usually gradual. Itching and burning are severe, and scratching often obscures the primary lesions with eczematization of nearby skin, leading to an erroneous diagnosis of eczema. Strict adherence to a gluten-free diet for prolonged periods may control the disease in some patients, obviating or reducing the requirement for drug therapy. Dapsone, sulfapyridine, and colchicines are sometimes prescribed for relief of itching.

Celiac Sprue (CS) is generally considered to be an autoimmune disease and the antibodies found in the serum of the patients support the theory that the disease is immunological in nature. Antibodies to tissue transglutaminase (tTGase or tTG) and gliadin appear in almost 100% of the patients with active CS, and the presence of such antibodies, particularly of the IgA class, has been used in diagnosis of the disease.

The large majority of patients express the HLA-DQ2 [DQ(a1*0501, b1*02)] and/or DQ8 [DQ(a1*0301, b1*0302)] molecules. It is believed that intestinal damage is caused by interactions between specific gliadin oligopeptides and the HLA-DQ2 or DQ8 antigen, which in turn induce proliferation of T lymphocytes in the sub-epithelial layers. T helper 1 cells and cytokines apparently play a major role in a local inflammatory process leading to villous atrophy of the small intestine.

At the present time, there is no good therapy for the disease, except to avoid completely all foods containing gluten. Although gluten withdrawal has transformed the prognosis for children and substantially improved it for adults, some people still die of the disease, mainly adults who had severe disease at the outset. A leading cause of death is lymphoreticular disease, especially intestinal lymphoma. It is not known whether a gluten-free diet diminishes this risk. Apparent clinical remission is often associated with histologic relapse that is detected only by review biopsies or by increased EMA titers.

Gluten is so widely used, for example, in commercial soups, sauces, ice creams, hot dogs, and other foodstuffs, that patients need detailed lists of foodstuffs to avoid and expert advice from a dietitian familiar with celiac disease. Ingesting even small amounts of gluten may prevent remission or induce relapse. Supplementary vitamins, minerals, and hematinics may also be required, depending on deficiency. A few patients respond poorly or not at all to gluten withdrawal, either because the diagnosis is incorrect or because the disease is refractory. In the latter case, oral corticosteroids (e.g., prednisone 10 to 20 mg bid) may induce response.

In view of the serious and widespread nature of Celiac Sprue and the difficulty of removing gluten from the diet, better methods of treatment are of great interest. In particular, there is a need for treatment methods that allow the Celiac Sprue individual to eat gluten-containing foodstuffs without ill effect or at least to tolerate such foodstuffs in small or moderate quantities without inducing relapse. The present invention meets this need for better therapies for Celiac Sprue by providing new drugs and methods and formulations of new and existing drugs to treat Celiac Sprue. International Patent Application US03/04743, herein specifically incorporated by reference, discloses aspects of gluten protease stability and immunogenicity.

SUMMARY OF THE INVENTION

In one aspect, the present invention provides methods for treating Celiac Sprue and/or dermatitis herpetiformis and the symptoms thereof by administration of a tTGase (tissue transglutaminase) inhibitor to the patient. In one embodiment, the tTGase inhibitor employed in the method is a small molecule tTGase inhibitor comprising a 3-halo-4,5-dihydroisoxazole moiety.

In another aspect, the present invention provides novel derivative compounds of 3-halo-4,5-dihydroisoxazoles and methods for treating Celiac Sprue and/or dermatitis herpetiformis by administering those compounds.

In one embodiment, the tTGase inhibitor employed in the method is an analog of isatin (2, 3 diketoindoline).

In another aspect, the invention provides pharmaceutical formulations comprising a tTGase inhibitor and a pharmaceutically acceptable carrier. In one embodiment, the formulation also comprises one or more glutenases, as described in U.S. Provisional Application No. 60/392,782 filed Jun. 28, 2002; and U.S. Provisional Application No. 60/428,033, filed Nov. 20, 2002, both of which are incorporated herein by reference. The invention also provides methods for the administration of enteric formulations of one or more tTGase inhibitors to treat Celiac Sprue. In another aspect, the tTGase inhibitors and/or pharmaceutical formulations of the present invention are useful in treating disorders where TGases are a factor in the disease etiology, where such disorders may include cancer, neurological disorders, wound healing, etc. These conditions include Alzheimer's and Huntington's diseases, where the TGases appear to be a factor in the formation of inappropriate proteinaceous aggregates that may be cytotoxic. In diseases such as progressive supranuclear palsy, Huntington's, Alzheimer's and Parkinson's diseases, the aberrant activation of TGases may be caused by oxidative stress and inflammation.

These and other aspects and embodiments of the invention and methods for making and using the invention are described in more detail in the description of the drawings and the invention, the examples, the claims, and the drawings that follow.

DETAILED DESCRIPTION OF THE EMBODIMENTS

Celiac Sprue and/or dermatitis herpetiformis are treated by inhibition of tissue transglutaminase. Methods and compositions are provided for the administration of one or more tTGase inhibitors to a patient suffering from Celiac Sprue and/or dermatitis herpetiformis. The compositions of the invention include formulations of tTGase inhibitors that comprise an enteric coating that allows delivery of the agents to the intestine in an active form; the agents are stabilized to resist digestion or alternative chemical transformations in acidic stomach conditions. In another embodiment, food is pretreated or combined with glutenase, or a glutenase is co-administered (whether in time or in a formulation of the invention) with a tTGase inhibitor of the invention The subject methods are useful for both prophylactic and therapeutic purposes. Thus, as used herein, the term "treating" is used to refer to both prevention of disease, and treatment of a pre-existing condition. The treatment of ongoing disease, to stabilize or improve the clinical symptoms of the patient, is a particularly important benefit provided by the present invention. Such treatment is desirably performed prior to loss of function in the affected tissues; consequently, the prophylactic therapeutic benefits provided by the invention are also important. Evidence of therapeutic effect may be any diminution in the severity of disease, particularly diminution of the severity of such symptoms as fatigue, chronic diarrhea, malabsorption of nutrients, weight loss, abdominal distension, and anemia. Other disease indicia include the presence of antibodies specific for glutens, antibodies specific for tissue transglutaminase, the presence of pro-inflammatory T cells and cytokines, and degradation of the villus structure of the small intestine. Application of the methods and compositions of the invention can result in the improvement of any and all of these disease indicia of Celiac Sprue.

Patients that can benefit from the present invention include both adults and children. Children in particular benefit from prophylactic treatment, as prevention of early exposure to toxic gluten peptides can prevent development of the disease into its more severe forms. Children suitable for prophylaxis in accordance with the methods of the invention can be identified by genetic testing for predisposition, e.g. by HLA typing; by family history, and by other methods known in the art. As is known in the art for other medications, and in accordance with the teachings herein, dosages of the tTGase inhibitors of the invention can be adjusted for pediatric use.

Compounds of interest for inhibition of tTGase include those having the general formulae

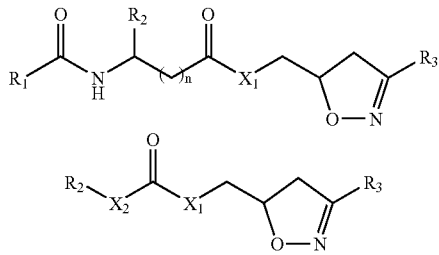

where $R_1$, $R_2$ and $R_3$ are independently selected from H, alkyl, alkenyl, cycloalkyl, aryl, heteroalkyl, heteroaryl, alkoxy, alkylthio, arakyl, aralkenyl, halo, haloalkyl, haloalkoxy, heterocyclyl, and heterocyclylalkyl groups. $R_1$ and $R_2$ can also be an amino acid, a peptide, a peptidomimetic, or a peptidic protecting groups.

Illustrative $R_1$ groups include Cbz, Fmoc, and Boc. In other embodiments of the invention, $R_1$ is an arylether, aryl, alkylether or alkyl group, e.g. O-benzyl, benzyl, methyl or ethyl.

$R_2$ groups of interest include OMe, OtBu, Gly, and Gly-$NH_2$, In other embodiments, $R_2$ is selected from the group consisting of (s)-Bn, (s)-$CO_2$Me, (s)-Me, (R)-Bn, (S)-$CH_2$CONHBn, (S)-(1H-inol-yl)-methyl, and (S)-(4-hydroxy-phenyl)-methyl.

$R_3$ is preferably a halo group, i.e. F, Cl, Br, and I.

$X_1$ and $X_2$ are selected from the group consisting of NH, O, and $NR_4$. where $R_4$ is a lower alkyl.

n is a whole number between 0 and 10, usually between 0 and 5, and more usually between 0 and 3.

The tTGase inhibitory compounds of the invention from the isoxazoles can be readily prepared using methods known in the art for other purposes and the teachings herein. Examples of synthetic routes to these compounds are also described in examples below For example, Castelhano et al have demonstrated that the dihydroisoxazole derivative (S)-1-[(3-Bromo-4,5-dihydro-isoxazol-5-ylmethyl)-carbamoyl]-2-phenyl-ethyl}-carbamic acid benzyl ester is an inhibitor of bovine epidermal transglutaminase (Castelhano et al., *Bioorg. Chem.* (1988) 16, 335-340). The following general formula for transglutaminase inhibitors is disclosed in EP0237082:

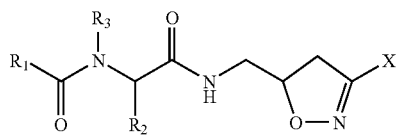

Here we identify new compounds within this genus that are especially effective inhibitors of human tissue transglutaminase, and may therefore be used to treat Celiac Sprue and/or Dermatitis Herpetiforms. We also disclose new compounds with comparable activity.

Another example of tTGase inhibitors are analogs of the dioxoindoline isatin. The cyclic α-keto amide structure of isatin serves as a good analog of γ-carboxamide group of tTGase glutamyl substrate. α-keto amides are widely utilized as reversible inhibitors of cysteine-dependent proteases and, in a similar way, the hetetocyclic structure of isatin possesses an electrophilic carbonyl group which could be recognized by the enzyme as an analog of the substrate γ-carboxamide carbonyl group. Using standard procedures known in the art, the aromatic portion of the isatin structure can be derivatized further to incorporate additional functional groups into the inhibitors mimicking the other parts of peptide substrates.

The illustrative compounds of the invention described above were tested in a tTGase assay with recombinant human tissue transglutaminase, which was expressed, purified and assayed as described (Piper et al., *Biochemistry* (2001) 41, 386-393). Competitive inhibition with respect to the Cbz-Gln-Gly substrate was observed for all substrates; in all cases irreversible inactivation of the enzyme was also observed.

To facilitate an appreciation of the invention, the tTGase inhibitors of the invention have in part been described above with structures containing variable "R" groups that are defined by reference to the various organic moieties that can be present at the indicated position in the structure. Below, brief definitions are provided for the phrases used to define the organic moieties listed for each R group.

As used herein, "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Unless stated otherwise specifically in the specification, the alkyl radical may be optionally substituted by hydroxy, alkoxy, aryloxy, haloalkoxy, cyano, nitro, mercapto, alkylthio, $-N(R^8)_2$, $-C(O)OR^8$, $-C(O)N(R^8)_2$ or $-N(R^8)C(O)R^8$ where each $R^8$ is independently hydrogen, alkyl, alkenyl, cycloalkyl, cycloalkylalkyl, aralkyl or aryl. Unless stated otherwise specifically in the specification, it is understood that for radicals, as defined below, that contain a substituted alkyl group that the substitution can occur on any carbon of the alkyl group.

"Alkoxy" refers to a radical of the formula $-OR_a$ where $R_a$ is an alkyl radical as defined above, e.g., methoxy, ethoxy, n-propoxy, 1-methylethoxy (iso-propoxy), n-butoxy, n-pentoxy, 1,1-dimethylethoxy (t-butoxy), and the like. Unless stated otherwise specifically in the specification, it is understood that for radicals, as defined below, that contain a substituted alkoxy group that the substitution can occur on any carbon of the alkoxy group. The alkyl radical in the alkoxy radical may be optionally substituted as described above.

"Alkylthio" refers to a radical of the formula $-SR_a$ where $R_a$ is an alkyl radical as defined above, e.g., methylthio, ethylthio, n-propylthio, 1-methylethylthio (iso-propylthio), n-butylthio, n-pentylthio, 1,1-dimethylethylthio (t-butylthio), and the like. Unless stated otherwise specifically in the specification, it is understood that for radicals, as defined below, that contain a substituted alkylthio group that the substitution can occur on any carbon of the alkylthio group. The alkyl radical in the alkylthio radical may be optionally substituted as described above.

"Alkenyl" refers to a straight or branched hydrocarbon chain radical consisting solely of carbon and hydrogen atoms, containing at least one double bond, having from two to eight carbon atoms, and which is attached to the rest of the molecule by a single bond or a double bond, e.g., ethenyl, prop-1-enyl, but-1-enyl, pent-1-enyl, penta-1,4-dienyl, and the like. Unless stated otherwise specifically in the specification, the alkenyl radical may be optionally substituted by hydroxy, alkoxy, haloalkoxy, cyano, nitro, mercapto, alkylthio, cycloalkyl, $-N(R^8)_2$, $-C(O)OR^8$, $-C(O)N(R^8)_2$ or $-N(R^8)-C(O)-R^8$ where each $R^8$ is independently hydrogen, alkyl, alkenyl, cycloalkyl, cycloalkylalkyl, aralkyl or aryl. Unless stated otherwise specifically in the specification, it is understood that for radicals, as defined below, that contain a substituted alkenyl group that the substitution can occur on any carbon of the alkenyl group.

"Aryl" refers to a phenyl or naphthyl radical. Unless stated otherwise specifically in the specification, the term "aryl" or the prefix "ar-" (such as in "aralkyl") is meant to include aryl radicals optionally substituted by one or more substituents selected from the group consisting of hydroxy, alkoxy, aryloxy, haloalkoxy, cyano, nitro, mercapto, alkylthio, cycloalkyl, $-N(R^8)_2$, $-C(O)OR^8$, $-C(O)N(R^8)_2$ or $-N(R^8)C(O)R^8$ where each $R^8$ is independently hydrogen, alkyl, alkenyl, cycloalkyl, cycloalkylalkyl, aralkyl or aryl. The term "aryl" also refers to the compound $C_6H_5$, i.e. Bn.

"Aralkyl" refers to a radical of the formula $-R_aR_b$ where $R_a$ is an alkyl radical as defined above and $R_b$ is one or more aryl radicals as defined above, e.g., benzyl, diphenylmethyl and the like. The aryl radical(s) may be optionally substituted as described above.

"Aralkenyl" refers to a radical of the formula $-R_cR_b$ where $R_c$ is an alkenyl radical as defined above and $R_b$ is one or more aryl radicals as defined above, e.g., 3-phenylprop-1-enyl, and the like. The aryl radical(s) and the alkenyl radical may be optionally substituted as described above.

"Alkylene chain" refers to a straight or branched divalent hydrocarbon chain consisting solely of carbon and hydrogen, containing no unsaturation and having from one to eight carbon atoms, e.g., methylene, ethylene, propylene, n-butylene, and the like. The alkylene chain may be optionally substituted by one or more substituents selected from the group consisting of aryl, halo, hydroxy, alkoxy, haloalkoxy, cyano, nitro, mercapto, alkylthio, cycloalkyl, $-N(R^8)_2$, $-C(O)OR^8$, $-C(O)N(R^8)_2$ or $-N(R^8)C(O)R^8$ where each $R^8$ is independently hydrogen, alkyl, alkenyl, cycloalkyl, cycloalkylalkyl, aralkyl or aryl. The alkylene chain may be attached to the rest of the molecule through any two carbons within the chain.

"Alkenylene chain" refers to a straight or branched divalent hydrocarbon chain consisting solely of carbon and hydrogen, containing at least one double bond and having from two to eight carbon atoms, e.g., ethenylene, prop-1-enylene, but-1-enylene, pent-1-enylene, hexa-1,4-dienylene, and the like. The alkenylene chain may be optionally substituted by one or more substituents selected from the group consisting of aryl, halo, hydroxy, alkoxy, haloalkoxy, cyano, nitro, mercapto, alkylthio, cycloalkyl, $-N(R^8)_2$, $-C(O)OR^8$, $-C(O)N(R^8)_2$ or $-N(R^8)C(O)R^8$ where each $R^8$ is independently hydrogen, alkyl, alkenyl, cycloalkyl, cycloalkylalkyl, aralkyl or aryl. The alkenylene chain may be attached to the rest of the molecule through any two carbons within the chain.

"Cycloalkyl" refers to a stable monovalent monocyclic or bicyclic hydrocarbon radical consisting solely of carbon and hydrogen atoms, having from three to ten carbon atoms, and which is saturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents independently selected from the group consisting of alkyl, aryl, aralkyl, halo, haloalkyl, hydroxy, alkoxy, haloalkoxy, cyano, nitro, mercapto, alkylthio, cycloalkyl, $-N(R^8)_2$, $-C(O)OR^8$, —C(O)N(R$^8$)$_2$ or —N(R$^8$)C(O)R$^8$ where each R$^8$ is independently hydrogen, alkyl, alkenyl, cycloalkyl, cycloalkylalkyl, aralkyl or aryl.

"Cycloalkylalkyl" refers to a radical of the formula —R$_a$R$_d$ where R$_a$ is an alkyl radical as defined above and R$_d$ is a cycloalkyl radical as defined above. The alkyl radical and the cycloalkyl radical may be optionally substituted as defined above.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Haloalkoxy" refers to a radical of the formula —OR$_c$ where R$_c$ is an haloalkyl radical as defined above, e.g., trifluoromethoxy, difluoromethoxy, trichloromethoxy, 2,2,2-trifluoroethoxy, 1-fluoromethyl-2-fluoroethoxy, 3-bromo-2-fluoropropoxy, 1-bromomethyl-2-bromoethoxy, and the like.

"Heterocyclyl" refers to a stable 3- to 15-membered ring radical which consists of carbon atoms and from one to five heteroatoms selected from the group consisting of nitrogen, oxygen and sulfur. For purposes of this invention, the heterocyclyl radical may be a monocyclic, bicyclic or tricyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be aromatic or partially or fully saturated. The heterocyclyl radical may not be attached to the rest of the molecule at any heteroatom atom. Examples of such heterocyclyl radicals include, but are not limited to, azepinyl, acridinyl, benzimidazolyl, benzthiazolyl, benzothiadiazolyl, benzoxazolyl, benzodioxolyl, benzodioxinyl, benzopyranyl, benzopyranonyl, benzofuranyl, benzofuranonyl, benzothienyl (benzothiophenyl), benzotriazolyl, carbazolyl, cinnolinyl, decahydroisoquinolyl, dioxolanyl, furanyl, furanonyl, isothiazolyl, imidazolyl, imidazolinyl, imidazolidinyl, isothiazolidinyl, indolyl, indazolyl, isoindolyl, indolinyl, isoindolinyl, indolizinyl, isoxazolyl, isoxazolidinyl, morpholinyl, naphthyridinyl, oxadiazolyl, octahydroindolyl, octahydroisoindolyl, 2-oxopiperazinyl, 2-oxopiperidinyl, 2-oxopyrrolidinyl, 2-oxoazepinyl, oxazolyl, oxazolidinyl, oxiranyl, piperidinyl, piperazinyl, 4-piperidonyl, phenazinyl, phenothiazinyl, phenoxazinyl, phthalazinyl, pteridinyl, purinyl, pyrrolyl, pyrrolidinyl, pyrazolyl, pyrazolidinyl, pyridinyl, pyrazinyl, pyrimidinyl, pyridazinyl, quinazolinyl, quinoxalinyl, quinolinyl, quinuclidinyl, isoquinolinyl, thiazolyl, thiazolidinyl, thiadiazolyl, triazolyl, tetrazolyl, tetrahydrofuryl, triazinyl, tetrahydropyranyl, thienyl, thiamorpholinyl, thiamorpholinyl sulfoxide, and thiamorpholinyl sulfone. Unless stated otherwise specifically in the specification, the term "heterocyclyl" is meant to include heterocyclyl radicals as defined above which are optionally substituted by one or more substituents selected from the group consisting of alkyl, halo, nitro, cyano, haloalkyl, haloalkoxy, aryl, heterocyclyl, heterocyclylalkyl, —OR$^8$, —R$^7$—OR$^8$, —C(O)OR$^8$, —R$^7$—C(O)OR$^8$, —C(O)N(R$^8$)$_2$, —N(R$^8$)$_2$, —R$^7$—N(R$^8$)$_2$, and —N(R$^8$)C(O)R$^8$ wherein each R$^7$ is a straight or branched alkylene or alkenylene chain and each R$^8$ is independently hydrogen, alkyl, alkenyl, cycloalkyl, cycloalkylalkyl, aralkyl or aryl.

"Heterocyclylalkyl" refers to a radical of the formula —R$_a$R$_e$ where R$_a$ is an alkyl radical as defined above and R$_e$ is a heterocyclyl radical as defined above, and if the heterocyclyl is a nitrogen-containing heterocyclyl, the heterocyclyl may be attached to the alkyl radical at the nitrogen atom. The heterocyclyl radical may be optionally substituted as defined above.

In the formulas provided herein, molecular variations are included, which may be based on isosteric replacement. "Isosteric replacement" refers to the concept of modifying chemicals through the replacement of single atoms or entire functional groups with alternatives that have similar size, shape and electro-magnetic properties, e.g. O is the isosteric replacement of S, N, COOH is the isosteric replacement of tetrazole, F is the isosteric replacement of H, sulfonate is the isosteric replacement of phosphate etc.

As used herein, compounds which are "commercially available" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.), Novabiochem and Argonaut Technology.

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., www.acs.org may be contacted for more details). Chemicals that are known but not commercially available in catalogs may be prepared by custom chemical synthesis houses, where many of the standard chemical supply houses (e.g., those listed above) provide custom synthesis services.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The tTGase inhibitors, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

The present invention provides the tTGase inhibitors in a variety of formulations for therapeutic administration. In one aspect, the agents are formulated into pharmaceutical compositions by combination with appropriate, pharmaceutically acceptable carriers or diluents, and are formulated into preparations in solid, semi-solid, liquid or gaseous forms, such as tablets, capsules, powders, granules, ointments, solutions, suppositories, injections, inhalants, gels, microspheres, and aerosols. As such, administration of the tTGase inhibitors is achieved in various ways, although oral administration is a preferred route of administration. In some formulations, the tTGase inhibitors are systemic after administration; in others, the inhibitor is localized by virtue of the formulation, such as the use of an implant that acts to retain the active dose at the site of implantation.

In some pharmaceutical dosage forms, the tTGase inhibitors are administered in the form of their pharmaceutically acceptable salts. In some dosage forms, the tTGase inhibitor is used alone, while in others, the tTGase is used in combination with another pharmaceutically active compounds. In the latter embodiment, the other active compound is, in some embodiments, a glutenase that can cleave or otherwise degrade a toxic gluten oligopeptide, as described in the Examples below. The following methods and excipients are merely exemplary and are in no way limiting.

For oral preparations, the agents are used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and in some embodiments, with diluents, buffering agents, moistening agents, preservatives and flavoring agents.

In one embodiment of the invention, the oral formulations comprise enteric coatings, so that the active agent is delivered to the intestinal tract. Enteric formulations are often used to protect an active ingredient from the strongly acid contents of the stomach. Such formulations are created by coating a solid dosage form with a film of a polymer that is insoluble in acid environments and soluble in basic environments. Exemplary films are cellulose acetate phthalate, polyvinyl acetate phthalate, hydroxypropyl methylcellulose phthalate and hydroxypropyl methylcellulose acetate succinate, methacrylate copolymers, and cellulose acetate phthalate.

Other enteric formulations of the tTGase inhibitors of the invention comprise engineered polymer microspheres made of biologically erodable polymers, which display strong adhesive interactions with gastrointestinal mucus and cellular linings, can traverse both the mucosal absorptive epithelium and the follicle-associated epithelium covering the lymphoid tissue of Peyer's patches. The polymers maintain contact with intestinal epithelium for extended periods of time and actually penetrate it, through and between cells. See, for example, Mathiowitz et al. (1997) *Nature* 386 (6623): 410-414. Drug delivery systems can also utilize a core of superporous hydrogels (SPH) and SPH composite (SPHC), as described by Dorkoosh et al. (2001) *J Control Release* 71(3):307-18.

In another embodiment, the tTGase inhibitor or formulation thereof is admixed with food, or used to pre-treat foodstuffs containing glutens.

Formulations are typically provided in a unit dosage form, where the term "unit dosage form," refers to physically discrete units suitable as unitary dosages for human subjects, each unit containing a predetermined quantity of tTGase inhibitor calculated in an amount sufficient to produce the desired effect in association with a pharmaceutically acceptable diluent, carrier or vehicle. The specifications for the unit dosage forms of the present invention depend on the particular complex employed and the effect to be achieved, and the pharmacodynamics associated with each complex in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Depending on the patient and condition being treated and on the administration route, the tTGase inhibitor is administered in dosages of 0.01 mg to 500 mg/kg body weight per day, e.g. about 100 mg/day for an average person. Dosages are appropriately adjusted for pediatric formulation. Those of skill will readily appreciate that dose levels can vary as a function of the specific inhibitor, the diet of the patient and the gluten content of the diet, the severity of the symptoms, and the susceptibility of the subject to side effects. Some of the inhibitors of the invention are more potent than others. Preferred dosages for a given inhibitor are readily determinable by those of skill in the art by a variety of means. A preferred means is to measure the physiological potency of a given compound.

The methods of the invention are useful in the treatment of individuals suffering from Celiac Sprue and/or dermatitis herpetiformis, by administering an effective dose of a tTGase inhibitor, through a pharmaceutical formulation, and the like. Diagnosis of suitable patients may utilize a variety of criteria known to those of skill in the art. A quantitative increase in antibodies specific for gliadin, and/or tissue transglutaminase is indicative of the disease. Family histories and the presence of the HLA alleles HLA-DQ2 [DQ (a1*0501, b1*02)] and/or DQ8 [DQ(a1*0301, b1*0302)] are indicative of a susceptibility to the disease. Moreover, as tTG plays an important role in other diseases, such as Huntington's disease and skin diseases in addition to dermatitis herpetiformis, a variety of formulated versions of the compounds of the invention (e.g. topical formulations, intravenous injections) are useful for the treatment of such medical conditions. These conditions include Alzheimer's and Huntington's diseases, where the TGases appear to be a factor in the formation of inappropriate proteinaceous aggregates that may be cytotoxic. In diseases such as progressive supranuclear palsy, Huntington's, Alzheimer's and Parkinson's diseases, the aberrant activation of TGases may be caused by oxidative stress and inflammation.

Therapeutic effect is measured in terms of clinical outcome, or by immunological or biochemical tests. Suppression of the deleterious T-cell activity can be measured by enumeration of reactive Th1 cells, by quantitating the release of cytokines at the sites of lesions, or using other assays for the presence of autoimmune T cells known in the art. Also both the physician and patient can identify a reduction in symptoms of a disease.

Various methods for administration are employed in the practice of the invention. In one preferred embodiment, oral administration, for example with meals, is employed. The dosage of the therapeutic formulation can vary widely, depending upon the nature of the disease, the frequency of administration, the manner of administration, the clearance of the agent from the patient, and the like. The initial dose can be larger, followed by smaller maintenance doses. The dose can be administered as infrequently as weekly or biweekly, or more often fractionated into smaller doses and administered daily, with meals, semi-weekly, and the like, to maintain an effective dosage level.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

EXAMPLE 1

Synthesis of Dihydroxyisoxazole Containing tTGase Inhibitors

Synthesis of {(S)-1-[(3-Bromo-4,5-dihydro-isoxazol-5-ylmethyl)-carbamoyl]-2-phenyl-ethyl}-carbamic acid benzyl ester (n=0, X=NH, $R_1$=BnO, $R_2$=(S)—Bn, $R_3$=Br) (49). N-Cbz-L-Phe (0.30 g, 1.0 mmol) and HOBt (0.15 g, 1.1 eq) were dissolved in 2 mL DMF. 3-Bromo-5-aminomethyl-4,5-dihydroisoazole (0.18 g, 1.0 eq), prepared following a reported procedure (Rohloff et al. (1992) Tetrahedron Lett. 33(22):3113-3116), was added to the solution cooled in an ice bath followed by EDCI (0.23 g, 1.2 eq). The ice bath was removed and the stirring was continued overnight. The solution was diluted with ethyl acetate and washed with sat. $NaHCO_3$ solution and brine. The organic layer was dried over $MgSO_4$ and filtered. The solvent was removed by evaporation and the residue was purified by $SiO_2$ chromatography to give the title compound as a white solid (0.24 g, 52%).

$^1$H NMR (CDCl$_3$, 200 MHz): δ=7.34-7.26(m, 8H), 7.17 (d, 2H, J=7.6 Hz), 6.19-6.09(m, 1H), 5.21-5.15(m, 1H), 5.09(s, 2H), 4.74-4.60(m, 1H), 4.41-4.36(m, 1H), 3.49-3.45 (m, 2H), 3.26-3.12(m, 1H), 3.07(d, 2H, J=6.8 Hz), 2.97-2.76(m, 1 H) MS (ESI): m/z=460.1 [M+H]$^+$, 482.2 [M+Na]$^+$

49

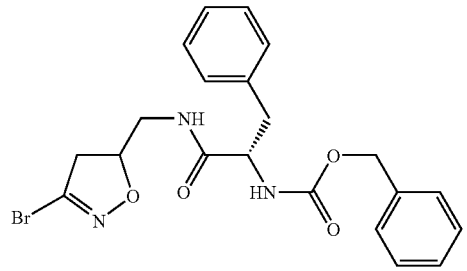

{(S)-1-[(3-Bromo-4,5-dihydro-isoxazol-5-ylmethyl)-carbamoyl]-2-phenyl-ethyl}-carbamic acid benzyl ester Synthesis of (S)-2-Benzyloxycarbonylamino-4-[(3-bromo-4,5-dihydro-isoxazol-5-ylmethyl)-carbamoyl]-butyric acid methyl ester (n=2, X=NH, $R_1$=BnO, $R_2$=(S)—$CO_2Me$, $R_3$=Br) (50). The title compound was prepared according to the procedure for compound 49 except using N-Cbz-L-Glu-OMe.

$^1$H NMR (CDCl$_3$, 200 MHz): δ=7.41-7.30(m, 5H), 6.22-6.12(m, 1H), 5.63-5.57(m, 1H), 5.11(s, 2H), 4.82-4.74(m, 1H), 4.41-4.33(m, 1H), 3.75(s, 3H), 3.54-3.48(m, 2H), 3.32-3.15(m, 1H), 3.02-2.88(m, 1H), 2.34-2.22(m, 3H), 2.05-1.94 (m, 1H) MS (ESI): m/z=456.1 [M+H]$^+$, 478.2 [M+Na]$^+$

50

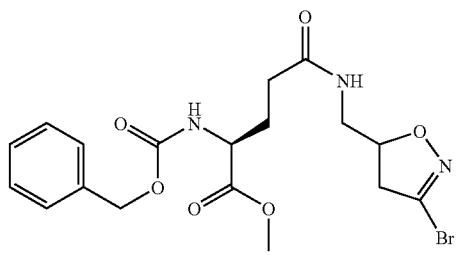

(S)-2-Benzyloxycarbonylamino-4-[(3-bromo-4,5-dihydro-isoxazol-5-ylmethyl)-carbamoyl]-butyric acid methyl ester Synthesis of (S)-2-Benzyloxycarbonylamino-N-(3-bromo-4,5-dihydro-isoxazol-5-ylmethyl)-succinamic acid methyl ester (n=1, X=NH, $R_1$=BnO, $R_2$=(S)—$CO_2Me$, R$_3$=Br) (51). The title compound was prepared according to the procedure for compound 49 except using N-Cbz-L-Asp-OMe.

$^1$H NMR (CDCl$_3$, 200 MHz): δ=7.37-7.30(m, 5H), 6.00-5.90(m, 2H), 5.13(s, 2H), 4.80-4.71(m, 1H), 4.63-4.58(m, 1H), 3.76(s, 3H), 3.54-3.44(m, 2H), 3.33-3.23(m, 1H), 2.99-2.70(m, 3H) MS (ESI): m/z=442.1 [M+H]$^+$, 464.2 [M+Na]$^+$

51

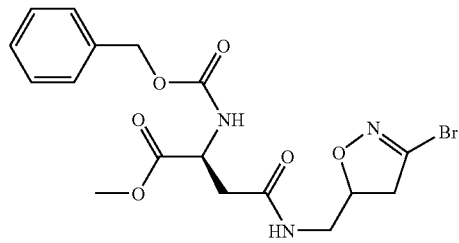

(S)-2-Benzyloxycarbonylamino-N-(3-bromo-4,5-dihydro-isoxazol-5-ylmethyl)-succinamic acid methyl ester Synthesis of (S)-2-Benzyloxycarbonylamino-3-phenyl-propionic acid 3-bromo-4,5-dihydro-isoxazol-5-ylmethyl ester (n=0, X=O, R$_1$=BnO, R$_2$=(S)—Bn, R$_3$=Br) (52). N-Cbz-L-Phe (0.30 g, 1.0 mmol) was dissolved in the mixture of acetonitrile (6 mL), DIEA (0.18 mL, 1.0 eq) and excess allyl bromide (3 mL). After the reaction was allowed to proceed overnight, the reaction mixture was diluted with ethyl acetate, washed with sat. Na$_2$CO$_3$ solution and brine, dried over MgSO$_4$ and concentrated to provide the ally ester as a clear oil (0.34 g, quant.). The ester (0.19 g, 0.57 mmol) and dibromoformaldoxime (0.14 g, 1.1 eq) were dissolved in 3 mL ethyl acetated and NaHCO$_3$ (0.21 g, 4.3 eq) was added to the solution. The reaction mixture was stirred overnight, diluted with ethyl acetated and washed with sat. NaHCO$_3$ solution and brine. The organic layer was dried over MgSO$_4$ and the solvent was removed by evaporation. The residue was purified by SiO$_2$ chromatography to give the title compound as a white solid (0.15 g, 58%)

$^1$H NMR (CDCl$_3$, 200 MHz): δ=7.35-7.26(m, 8H), 7.16-7.14(m, 2H), 5.20-5.05(m, 1H), 485-4.79(m, 1H), 4.68-4.63 (m, 1H), 4.22-4.15(m, 2H), 3.27-3.09(m, 3H), 2.96-2.77(m, 1H) MS (ESI): m/z=461.1 [M+H]$^+$, 483.2 [M+Na]$^+$

52

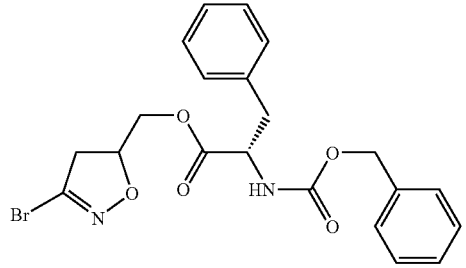

(S)-2-Benzyloxycarbonylamino-3-phenyl-propionic acid 3-bromo-4,5-dihydro-isoxazol-5-ylmethyl ester Synthesis of {(S)-1-[(3-Bromo-4,5-dihydro-isoxazol-5-ylmethyl)-carbamoyl]-ethyl}-carbamic acid benzyl ester (n=0, X=NH, R$_1$=BnO, R$_2$=(S)—Me, R$_3$=Br) (53). The title compound was prepared according to the procedure for compound 49 except using N-Cbz-L-Ala.

$^1$H NMR (CDCl$_3$, 200 MHz): δ=7.37-7.34(b, 5H), 6.68-6.45(m, 1H), 5.24-518(m, 1H), 5.13(s, 2H), 4.80-4.76(m, 1H), 4.26-4.18(m, 1H), 3.55-3.47(m, 2H), 3.33-3.19(m, 1H), 1.39(d, 3H, J=7.0 Hz) MS (ESI): m/z=384.1 [M+H]$^+$, 406.1 [M+Na]$^+$

53

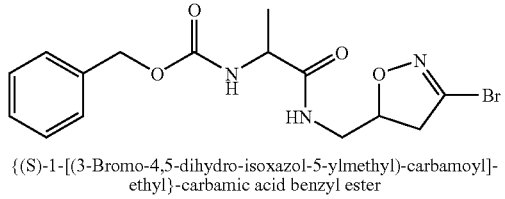

{(S)-1-[(3-Bromo-4,5-dihydro-isoxazol-5-ylmethyl)-carbamoyl]-ethyl}-carbamic acid benzyl ester Synthesis of (S)-2-Acetylamino-N-(3-bromo-4,5-dihydro-isoxazol-5-ylmethyl)-3-phenyl-propionamide (n=0, X=NH, R$_1$=Me, R$_2$=(S)—Bn, R$_3$=Br) (54). The title compound was prepared according to the procedure for compound 49 except using N-Ac-L-Phe.

$^1$H NMR (CDCl$_3$, 200 MHz): δ=7.33-7.18(m, 5H), 6.14-6.09(m, 1H), 6.02-5.97(m, 1H), 4.67-4.59(m, 2H), 3.49-3.41 (m, 2H), 3.22-3.03(m, 3H), 2.97-2.70(m, 1H), 2.00(s, 3H) MS (ESI): m/z=368.1 [M+H]$^+$, 390.2 [M+Na]$^+$

54

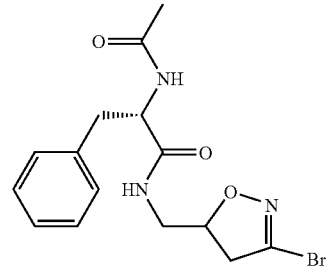

(S)-2-Acetylamino-N-(3-bromo-4,5-dihydro-isoxazol-5-ylmethyl)-3-phenyl-propionamide Synthesis of {(R)-1-[(3-Bromo-4,5-dihydro-isoxazol-5-ylmethyl)-carbamoyl]-2-phenyl-ethyl}-carbamic acid benzyl ester (n=0, X=NH, R$_1$=BnO, R$_2$=(R)—Bn, R$_3$=Br) (55). The title compound was prepared according to the procedure for compound 49 except using N-Cbz-D-Phe.

$^1$H NMR (CDCl$_3$, 200 MHz): δ=7.34-7.26(m, 8H), 7.17 (d, 2H, J=7.8 Hz), 6.19-6.09(m, 1H), 5.21-5.15(m, 1H), 5.09(s, 2H), 4.74-4.60(m, 1H), 4.41-4.36(m, 1H), 3.49-3.45 (m, 2H), 3.26-3.12(m,1H), 3.07(d, 2H, J=7.0 Hz), 2.97-2.76 (m, 1H) MS (ESI): m/z=460.1 [M+H]$^+$, 482.2 [M+Na]$^+$

55

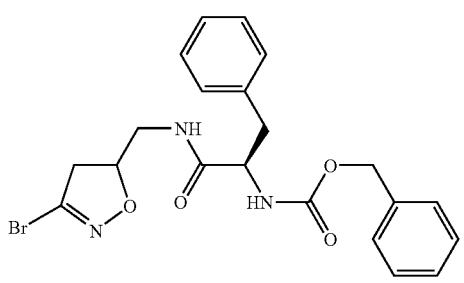

{(R)-1-[(3-Bromo-4,5-dihydro-isoxazol-5-ylmethyl)-carbamoyl]-2-phenyl-ethyl}-carbamic acid benzyl ester Synthesis of {(S)-2-Benzylcarbamoyl-1-[(3-bromo-4,5-dihydro-isoxazol-5-ylmethyl)-carbamoyl]-ethy}-carbamic acid benzyl ester (n=0, X=NH, R$_1$=BnO, R$_2$=(S)—CH$_2$CONHBn, R$_3$=Br) (56). The title compound was prepared according to the procedure for compound 49 except using β-bezylamide of N-Cbz-L-Asp ((S)-N-Benzyl-2-benzyloxycarbonylamino-succinamic acid).

¹H NMR (CDCl₃, 400 MHz): δ=7.38-7.24(m, 11H), 6.43-6.40(m, 1H), 6.01-5.99(m, 1H), 5.14(s, 2H), 4.80-4.70(m, 1H), 4.58-4.52(m, 1H), 4.41(d, 2H, J=6.4 Hz), 3.57-3.50(m, 2H), 3.25-3.12(m, 1H), 3.00-3.94(m, 2H), 2.62-2.56(m, 1H) MS (ESI): m/z=517.1 [M+H]⁺, 539.2 [M+Na]⁺

¹H NMR (CDCl₃, 400 MHz): δ=7.34-7.26(m, 8H), 7.18-7.16(m, 2H), 5.57-5.56(m, 1H), 5.12-5.05(m, 2H), 4.93-4.73 (m, 2H), 3.80-3.67(m, 1H), 3.36-3.17(m, 2H), 3.02-3.86(m, 6H) MS (ESI): m/z=474.2 [M+H]⁺, 496.3 [M+Na]⁺

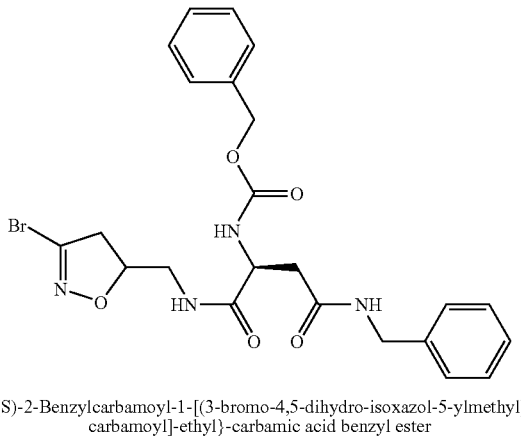

56

{(S)-2-Benzylcarbamoyl-1-[(3-bromo-4,5-dihydro-isoxazol-5-ylmethyl)-carbamoyl]-ethyl}-carbamic acid benzyl ester

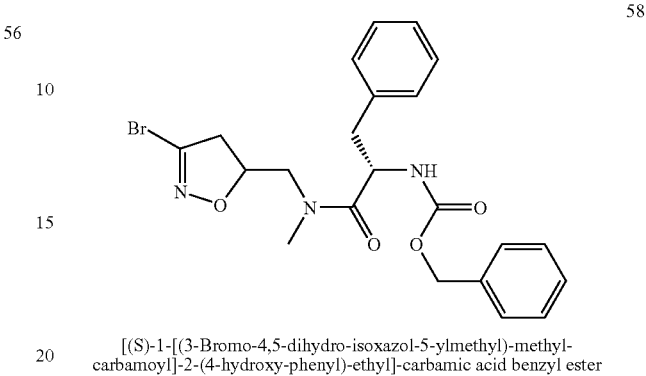

58

[(S)-1-[(3-Bromo-4,5-dihydro-isoxazol-5-ylmethyl)-methyl-carbamoyl]-2-(4-hydroxy-phenyl)-ethyl]-carbamic acid benzyl ester Synthesis of [(S)-1-[(3-Bromo-4,5-dihydro-isoxazol-5-ylmethyl)-carbamoyl]-2-(1H-indol-3-yl)-ethyl]-carbamic acid benzyl ester (n=0, X=NH, R₁=BnO, R₂=(S)—(1H-indol-3-yl)-methyl, R₃=Br) (57). The title compound was prepared according to the procedure for compound 49 except using N-Cbz-L-Trp.

¹H NMR (CDCl₃, 400 MHz): δ=8.14(br, 1H), 7.70-7.63 (m, 1H), 7.37-7.31(m, 6H), 7.22-7.18(m, 1H), 7.13-7.09(m, 1H), 7.04-7.02(m, 1H), 6.15-6.10(m, 1H), 5.45-5.39(m, 1H), 5.14-5.06(m, 2H), 4.59-4.47(m, 2H), 3.40-3.31(m, 3H), 3.20-3.14(m, 1H), 3.11-3.04(m, 1H), 2.82-2.74(m, 1H) MS (ESI): m/z=499.0 [M+H]⁺, 521.2 [M+Na]⁺

Synthesis of [(S)-1-[(3-Bromo-4,5-dihydro-isoxazol-5-ylmethyl)-methyl-carbamoyl]-2-(4-hydroxy-phenyl)-ethyl]-carbamic acid benzyl ester (n=0, X=NH, R₁=BnO, R₂=(S)-(4-hydroxy-phenyl)-methyl, R₃=Br) (59). The title compound was prepared according to the procedure for compound 49 except using N-Cbz-L-Tyr.

¹H NMR (DMSO-d₆, 400 MHz): δ=9.17(br, 1H), 8.27-8.23(m, 1H), 7.43-7.40(m, 1H), 7.32-7.22(m, 5H), 7.03(d, 2H, J=7.6 Hz), 6.62(d, 2H, J=7.6 Hz), 4.93(s, 2H), 4.68-4.64(m, 1H), 4.13-4.11(m, 1H), 3.37-3.19(m, 3H), 3.05-2.90 (m, 1H), 2.81-2.77(m, 1H), 2.63-2.58(m, 1H) MS (ESI): m/z=476.1 [M+H]⁺, 498.2 [M+Na]⁺

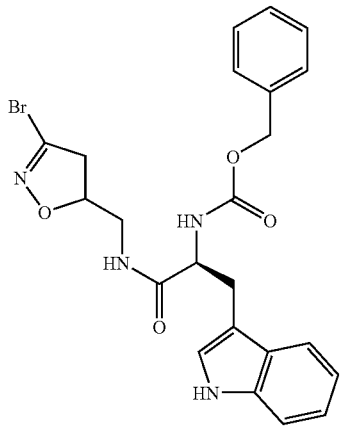

57

[(S)-1-[(3-Bromo-4,5-dihydro-isoxazol-5-ylmethyl)-carbamoyl]-2-(1H-indol-3-yl)-ethyl]-carbamic acid benzyl ester

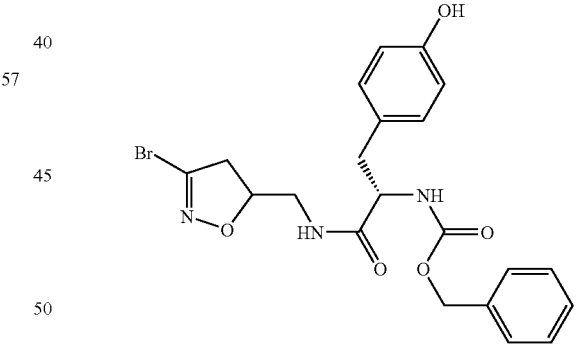

59

[(S)-1-[(3-Bromo-4,5-dihydro-isoxazol-5-ylmethyl)-methyl-carbamoyl]-2-(4-hydroxy-phenyl)-ethyl]-carbamic acid benzyl ester Synthesis of {(S)-1-[(3-Bromo-4,5-dihydro-isoxazol-5-ylmethyl)-methyl-carbamoyl]-2-phenyl-ethyl}-carbamic acid benzyl ester (n=0, X=NMe, R₁=BnO, R₂=(S)—Bn, R₃=Br) (58). The title compound was prepared according to the procedure for compound 52 except using N-methylallylamine.

Synthesis of 1-(3-Bromo-4 5-dihydro-isoxazol-5-ylmethyl)-3-phenyl-urea (X₁=NH, X₂=NH, R₂=Ph, R₃=Br) (60). 3-Bromo-5-aminomethyl-4,5-dihydroisoazole (20 mg, 0.11 mmol) and phenyl isocyanate (13 uL, 1.0 eq) were dissolved in the mixture of THF (0.5 mL) and DMF (0.1 mL). After 30 min of stirring, the mixture was diluted with ethyl acetate and washed with brine. The organic layer was dried over Na₂SO₄ and the solvents were removed by evaporation. The residue was purified by SiO₂ chromatography to give the title compound.

¹H NMR (acetone-d₆, 400 MHz): δ=8.02(br, 1H), 7.50(d, 2H), 7.25-7.20(m, 2H), 6.93(t, 1H), 6.24(br, 1H), 4.90-4.86

(m, 1H), 3.56-3.54(m, 2H), 3.48-3.41(m, 1H), 3.19-3.13(m, 1H) MS (ESI): m/z=298.0 [M+H]+

Synthesis of 1-(3-Bromo-4,5-dihydro-isoxazol-5-ylmethyl)-3-(2-chloro-5-trifluoromethyl-phenyl)-urea ($X_1$=NH, $X_2$=NH, $R_2$=2-chloro-5-trifluoromethyl-phenyl, $R_3$=Br) (61). The title compound was prepared according to the procedure for compound 60 except using 2-chloro-5-trifluoromethyl-phenylisocyanate $^1$H NMR (acetone-$d_6$, 400 MHz): δ=8.82(s, 1H), 8.12(br, 1H), 7.62(d, 1H, J=8.0 Hz), 7.30(d, 1H, J=8.0 Hz), 6.90(br, 1H), 4.93-4.87(m, 1H), 3.57-3.54(m, 2H), 3.49-3.42(m, 1H), 3.20-3.14(m, 1H) MS (ESI): m/z=400.0 [M+H]+

Synthesis of 1-(3-Bromo-4,5-dihydro-isoxazol-5-ylmethyl)-3-(4-chloro-2-trifluoromethyl-phenyl)-urea ($X_1$=NH, $X_2$=NH, $R_2$=4-chloro-2-trifluoromethyl-phenyl, $R_3$=Br) (62). The title compound was prepared according to the procedure for compound 60 except using 4-chloro-2-trifluoromethyl-phenylisocyanate.

$^1$H NMR (acetone-$d_6$, 400 MHz): δ=8.20(d, 1H, J=7.6 Hz), 7.66(br, 1H), 7.62-7.60(m, 2H), 6.82(br, 1H), 4.89-4.85 (m, 1H), 3.55-3.51(m, 2H), 3.47-3.40(m, 1H), 3.18-3.12(m, 1H) MS (ESI): m/z=400.0 [M+H]+

Synthesis of 1-(3-Bromo-4,5-dihydro-isoxazol-5-ylmethyl)-3-(4-fluoro-phenyl)-urea ($X_1$=NH, $X_2$=NH, $R_2$=4-fluoro-phenyl, $R_3$=Br) (63). The title compound was prepared according to the procedure for compound 60 except using 4-fluoro-phenylisocyanate.

$^1$H NMR (acetone-$d_6$, 200 MHz): δ=8.06(br, 1H), 7.47-7.40(m, 2H), 6.99-6.90(m, 2H), 5.94(br, 1H), 4.82-4.76(m, 1H), 3.45-3.30(m, 3H), 3.17-3.04(m, 1H) MS (ESI): m/z=316.0 [M+H]+

Synthesis of 1-(3-Bromo-4,5-dihydro-isoxazol-5-ylmethyl)-3-(2,5-dimethyl-phenyl)-urea ($X_1$=NH, $X_2$=NH, $R_2$=2,5-dimethyl-phenyl, $R_3$=Br) (64). The title compound was prepared according to the procedure for compound 60 except using 2,5-dimethyl-phenylisocyanate.
MS (ESI): m/z=326.0 [M+H]+

EXAMPLE 2

Synthesis of Dioxoindole Containing tTGase Inhibitors

Synthesis of 2,3-Dioxo-2,3-dihydro-1H-indole-5-sulfonic acid propylamide. 2,3-Dioxo-2,3-dihydro-1H-indole-5-sulfonyl chloride (0.10 g, 0.41 mmol), prepared by the reaction of the sodium salt of 5-isatinsulfonic acid with $POCl_3$, was dissolved in 5 mL THF. This solution was cooled in an ice bath and DIEA (0.14 mL, 2.0 eq) was added slowly, followed by n-propylamine (35 uL, 1.0 eq). Stirring was continued for 40 min and the solution was diluted with ethyl acetate and washed with brine. The organic layer was dried over $Na_2SO_4$ and the solvent was removed by evaporation. The residue was purified by $SiO_2$ chromatography to give the title compound (65 mg, 60%).

$^1$H NMR ($CD_3CN$, 400 MHz): δ=9.17(br, 1H), 8.02(d, 1H, J=8.0 Hz), 7.93(s, 1H), 7.13(d, 1H, J=8.0 Hz), 5.62-5.58(m, 1H), 2.85-2.80(m, 2H), 1.48-1.42(m, 2H), 0.85(t, 3H, J=7.2 Hz) MS (ESI): m/z=-267.1 [M-H]-

Synthesis of 2,3-Dioxo-2,3-dihydro-1H-indole-5-sulfonic acid benzylamide. The title compound was prepared from benzyl amine following the procedure for 2,3-Dioxo-2,3-dihydro-1H-indole-5-sulfonic acid propylamide.

$^1$H NMR ($CD_3CN$, 400 MHz): δ=9.19(br, 1H), 7.98(d, 1H, J=8.4 Hz), 7.85(s, 1H), 7.31-7.21(m, 5H), 7.07(d, 1H, J=8.4 Hz), 6.11(t, 1H, J=6.3 Hz), 4.11(d, 2H, J=6.3 Hz) MS (ESI): m/z=-315.2 [M-H]-

Synthesis of (S)-1-(2,3-Dioxo-2,3-dihydro-1H-indole-5-sulfonyl)-pyrrolidine-2-carboxylic acid methyl ester. The title compound was prepared from L-Pro-OMe following the procedure for 2,3-Dioxo-2,3-dihydro-1H-indole-5-sulfonic acid propylamide.

$^1$H NMR ($CDCl_3$, 200 MHz): δ=8.85(br, 1H), 8.15-8.11 (m, 2H), 7.11(d, 1H, J=8.8 Hz), 4.47-4.41(m, 1H), 3.74(s, 3H), 3.45-3.39(m, 2H), 2.20-1.94(m, 4H) MS (ESI): m/z=338.9 [M+H]+

Synthesis of (S)-2-(2,3-Dioxo-2,3-dihydro-1H-indole-5-sulfonylamino)-3-phenyl-propionamide. The title compound was prepared from L-Phe-$NH_2$ following the procedure for 2,3-Dioxo-2,3-dihydro-1H-indole-5-sulfonic acid propylamide.

$^1$H NMR ($CD_3CN$, 200 MHz): δ=10.70(br, 1H), 7.78(d, 1H, J=8.4 Hz), 7.64(s, 1H), 7.15-7.06(m, 6H), 6.90(d, 1H, J=8.4 Hz), 6.79(br, 1H), 6.08(br, 1H), 3.98-3.87(m, 1H), 3.04-2.95(m, 1H), 2.76-2.64(m,1H) MS (ESI): m/z=-372.2 [M-H]-

Synthesis of (S)-N-(2-Dimethylamino-ethyl)-2-(2,3-dioxo-2,3-dihydro-1H-indole-5-sulfonyl amino)-3-phenyl-propionamide. The title compound was prepared from L-Phe-$NHCH_2CH_2NMe_2$ following the procedure for 2,3-Dioxo-2,3-dihydro-1H-indole-5-sulfonic acid propylamide.

$^1$H NMR ($CD_3CN$, 400 MHz): δ=7.84(d, 1H, J=8.0 Hz), 7.69(s, 1H), 7.22-7.12(m, 6H), 6.98(d, 1H, J=8.0 Hz), 6.76 (br, 1H), 3.96-3.93(m, 1H), 3.10-3.02(m, 2H), 3.00-2.95(m, 1H), 2.78-2.72(m, 1H), 2.22-2.17(m, 2H), 2.15(s, 6H) MS (ESI): m/z=445.2 [M+H]+

Synthesis of 6-Bromo-7-methyl-1H-indole-2,3-dione. Chloral alcoholate (0.43 g, 1.05 eq) and $Na_2SO_4$ (2.84 g, 20 mmol) were dissolved in 10 mL water. 3-Bromo-2-methylaniline (0.33 g, 1.77 mmol) was added to the solution followed by 0.16 mL conc. HCl aqueous solution and $NH_2OH \cdot HCl$ (0.38 g, 3.0 eq). The mixture was refluxed for 15 min and stirring was continued for additional 1 hr at RT. The precipitate was collected by filtration, washed with water and dried under vacuum. This precipitate was dissolved in 1 mL $H_2SO_4$ and the solution was heated (80° C.) for 15 min. After cooling down to RT, the mixture was poured into ice-water mixture and the precipitate was collected, washed with water and dried under vacuum to give the title compound (0.26 g, 61%).

$^1$H NMR ($CD_3CN$, 200 MHz): δ=9.02(BR, 1h), 7.38(d, 1H, J=7.8 Hz), 7.30(d, 1H, J=7.8 Hz), 2.30(s, 3H) MS (ESI): m/z=-238.2 [M-H]-

Synthesis of 7-Methyl-6-phenyl-1H-indole-2,3-dione. 6-Bromo-7-methyl-1H-indole-2,3-dione (100 mg, 0.38 mmol) and phenylboronic acid (53 mg, 1.1 eq) were dissolved in 10 mL DME. $Pd(PPh_3)_4$ (22 mg, 0.05 eq) were added followed by $NaHCO_3$ (65 mg, 2.0 eq) dissolved in 10 mL water. The mixture was refluxed for 2.5 hr and the organic solvent was removed by evaporation. The mixture was extracted with ethyl acetate and the combined organic layers were dried over $Na_2SO_4$ and purified by $SiO_2$ chromatography to give the title compound (50 mg, 51%).

$^1$H NMR ($CDCl_3$, 400 MHz): δ=8.53(br, 1H), 7.52(d, 1H, J=7.6 Hz), 7.49-7.43(m, 3H), 7.31(d, 2H, J=6.4 Hz), 7.03(d, 1H, J=7.6 Hz), 2.16(s, 3H) MS (ESI): m/z=-236.3 [M-H]-

Inhibition of tTG. tTG (9 μM) was inactivated in 200 mM MOPS, pH=7.1, 5 mM $CaCl_2$, 1 mM ETDA at 30° C. containing 0-600 μM Pro-Gln-Pro-Aci-Leu-Pro-Tyr. Every 20 minutes a 40 μl aliquot was removed and residual tTG activity was assayed in 0.5 ml reaction containing 200 mM MOPS, pH=7.1, 5 mM $CaCl_2$, 1 mM ETDA, 10 mM α-ketoglutarate, 180 U/ml glutamate dehydrogenase (Biozyme laboratories) at 30° C. for 20 minutes by measuring the decrease of absorption at 340 nm. Residual activity was corrected by the corresponding uninhibited tTG reaction (0 µM inhibitor) and fitted to an exponential decay. Kinetic parameters were obtained by double-reciprocal plotting of the apparent second-order inactivation constant or, for isatin analogs, by fitting the data for reversible inhibitors to a standard Michaelis Menten equation with a competitive inhibition constant. The results of these inhibition experiments are shown in Tables 1 and 2 below.

TABLE 1

Tissue transglutaminase inhibition by dihydroisoxazoles

| Tested Compound | $K_I$ (M) | $k_{inh}$ (min$^{-1}$) | $k_{inh}/K_I$ (min$^{-1}$M$^{-1}$) |
|---|---|---|---|
| {(S)-1-[(3-Bromo-4,5-dihydro-isoxazol-5-ylmethyl)-carbamoyl]-2-phenyl-ethyl}-carbamic acid benzyl ester (49) | $0.73 \times 10^{-3}$ | 1.4 | 1900 |
| (S)-2-Benzyloxycarbonylamino-4-[(3-bromo-4,5-dihydro-isoxazol-5-ylmethyl)-carbamoyl]-butyric acid methyl ester (50) | $1.6 \times 10^{-3}$ | 0.32 | 200 |
| (S)-2-Benzyloxycarbonylamino-N-(3-bromo-4,5-dihydro-isoxazol-5-ylmethyl)-succinamic acid methyl ester (51) | $0.87 \times 10^{-3}$ | 0.43 | 490 |
| (S)-2-Benzyloxycarbonylamino-3-phenyl-propionic acid 3-bromo-4,5-dihydro-isoxazol-5-ylmethyl ester (52) | $1.3 \times 10^{-3}$ | 0.32 | 230 |
| {(S)-1-[(3-Bromo-4,5-dihydro-isoxazol-5-ylmethyl)-carbamoyl]-ethyl}-carbamic acid benzyl ester (53) | $0.91 \times 10^{-3}$ | 0.41 | 450 |
| (S)-2-Acetylamino-N-(3-bromo-4,5-dihydro-isoxazol-5-ylmethyl)-3-phenyl-propionamide (54) | $2.7 \times 10^{-3}$ | 0.60 | 220 |
| {(R)-1-[(3-Bromo-4,5-dihydro-isoxazol-5-ylmethyl)-carbamoyl]-2-phenyl-ethyl}-carbamic acid benzyl ester (55) | $0.31 \times 10^{-3}$ | 0.29 | 940 |
| {(S)-2-Benzylcarbamoyl-1-[(3-bromo-4,5-dihydro-isoxazol-5-ylmethyl)-carbamoyl]-ethyl}-carbamic acid benzyl ester (56) | $0.24 \times 10^{-3}$ | 0.54 | 2300 |
| [(S)-1-[(3-Bromo-4,5-dihydro-isoxazol-5-ylmethyl)-carbamoyl]-2-(1H-indol-3-yl)-ethyl]-carbamic acid benzyl ester (57) | $0.31 \times 10^{-3}$ | 0.78 | 2500 |
| {(S)-1-[(3-Bromo-4,5-dihydro-isoxazol-5-ylmethyl)-methyl-carbamoyl]-2-phenyl-ethyl}-carbamic acid benzyl ester (58) | $0.26 \times 10^{-3}$ | 0.19 | 730 |
| [(S)-1-[(3-Bromo-4,5-dihydro-isoxazol-5-ylmethyl)-methyl-carbamoyl]-2-(4-hydroxy-phenyl)-ethyl]-carbamic acid benzyl ester (59) | $0.42 \times 10^{-3}$ | 0.86 | 2000 |
| 1-(3-Bromo-4,5-dihydro-isoxazol-5-ylmethyl)-3-phenyl-urea (60) | $1.1 \times 10^{-3}$ | 0.89 | 810 |
| 1-(3-Bromo-4,5-dihydro-isoxazol-5-ylmethyl)-3-(2-chloro-5-trifluoromethyl-phenyl)-urea (61) | $0.91 \times 10^{-3}$ | 0.95 | 1000 |
| 1-(3-Bromo-4,5-dihydro-isoxazol-5-ylmethyl)-3-(4-chloro-2-trifluoromethyl-phenyl)-urea (62) | $1.3 \times 10^{-3}$ | 1.1 | 850 |
| 1-(3-Bromo-4,5-dihydro-isoxazol-5-ylmethyl)-3-(4-fluoro-phenyl)-urea (63) | $1.3 \times 10^{-3}$ | 1.0 | 770 |
| 1-(3-Bromo-4,5-dihydro-isoxazol-5-ylmethyl)-3-(2,5-dimethyl-phenyl)-urea (64) | $0.96 \times 10^{-3}$ | 0.97 | 1000 |

TABLE 2

Tissue transglutaminase inhibition by Istatin derivatives

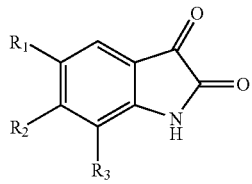

| Tested compound (R) | $K_I$ (M) |
|---|---|
| R1 = R2 = R3 = H | $8.6 \times 10^{-4}$ |
| R2 = R3 = H, R1 = NO$_2$ | $4.8 \times 10^{-5}$ |
| R2 = R3 = H; R1 = I | $2.2 \times 10^{-5}$ |
| R2 = R3 = H; R1 = F | $1.8 \times 10^{-5}$ |
| R1 = R2 = H; R3 = Ph | $4 \times 10^{-4}$ |
| R1 = R3 = H; R2 = Ph | $3.5 \times 10^{-4}$ |

The above results demonstrate that the compounds tested have tTGase inhibitory activity.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Moreover, due to biological functional equivalency considerations, changes can be made in protein structure without affecting the biological action in kind or amount. All such modifications are intended to be included within the scope of the appended claims.

What is claimed is:

1. A method of treating Celiac Sprue, the method comprising:
   orally administering to a patient an effective dose of 0.01 mg to 500 mg/kg body weight per day of a tissue transglutaminase (tTGase) inhibitor wherein said tTGase inhibitor has the formula:

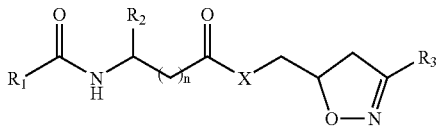

wherein $R_1$ is selected from arylether, aryl, alkylether or alkyl group;
   $R_2$ is selected from the group consisting of (S)-Bn, (S)-CO$_2$Me, (S)-Me, (R)-Bn, (S)-CH$_2$CONHBn, (S)-(1H-indol-yl)-methyl, and (S)-(4-hydroxy-phenyl)-methyl;
   $R_3$ is selected from F, I, Cl, and Br;
   n is from 0 to 3; and X is selected from the group consisting of O and NH,
   wherein said tTGase inhibitor attenuates gluten toxicity in said patient.

2. The method of claim 1, wherein said tTGase inhibitor is administered with a glutenase.

3. The method according to claim 1, wherein said tTGase inhibitor is contained in a formulation that comprises an enteric coating.

4. A method of treating Celiac Sprue, the method comprising:
   orally administering to a patient an effective dose of 0.01 mg to 500 mg/kg body weight per day of a tissue transglutaminase (tTGase) inhibitor, wherein said tTGase inhibitor has the formula:

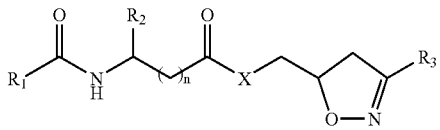

wherein $R_1$ and $R_2$ are independently selected from H, alkyl, alkenyl, cycloalkyl, aryl, heteroalkyl, heteroaryl, alkoxy, alkylthio, arakyl, aralkenyl, halo, haloalkyl, haloalkoxy, heterocyclyl, and heterocyclylalkyl groups, an amino acid, a peptide, a peptidomimetic, or a peptidic protecting group; wherein $R_2$ can additionally be selected from the group consisting of (SEQ ID NO:1) LPYPQPQLPY, (SEQ ID NO:2) LPF-PQPQLPF-NH$_2$, (SEQ ID NO:3) LPYPQPQLP, (SEQ ID NO:4) LPYPQPQLPYPQPQPF, LP-X$_{2-15}$ where X$_{2-15}$ is a peptide consisting of any 2-15 amino acid residues followed by a C-terminal proline; $R_3$ is selected from F, I, Cl, and Br; n is from 0 to 10; and X is selected from the group consisting of O and NH, wherein said tTGase inhibitor attenuates gluten toxicity in said patient.

5. The method of claim 4, wherein $R_1$ is selected from the group consisting of BnO, Me, Cbz, Fmoc, Boc, PQP, Ac-PQP, (SEQ ID NO:5) PQPQLPYPQP, (SEQ ID NO:6) Ac-PQPQLPFPQP, (SEQ ID NQ:7) QLQPFPQP, (SEQ ID NO:8) LQLQPFPQPLPYPQP, X$_{2-15}$-P, where X$_{2-15}$ is a peptide consisting of any 2-15 amino acid residues followed by a N-terminal proline.

6. The method of claim 4, wherein $R_2$ is selected from the group consisting of (S)-Bn, (S)-CO$_2$Me, (S)-Me, (R)-Bn, (S)-CH$_2$CONHBn, (S)-(1H-inol-yl)-methyl, (S)-(4-hydrohy-phenyl)-methyl, OMe, OtBu, Gly, Gly-NH$_2$, LPY, LPF-NH$_2$.

7. The method according to claim 4, wherein said tTGase inhibitor is selected from the group consisting of:
   {(S)-1-[(3-Bromo-4,5-dihydro-isoxazol-5-ylmethyl)-carbamoyl]-2-phenyl-ethyl}-carbamic acid benzyl ester; (S)-2-Benzyloxycarbonylamino-4-[(3-bromo-4,5-dihydro-isoxazol-5-ylmethyl)-carbamoyl]-butyric acid methyl ester; (S)-2-Benzyloxycarbonylamino-N-(3-bromo-4,5-dihydro-isoxazol-5-ylmethyl)-succinamic acid methyl ester; (S)-2-Benzyloxycarbonylamino-3-phenyl-propionic acid 3-bromo-4,5-dihydro-isoxazol-5-ylmethyl ester; {(S)-1-[(3-Bromo-4,5-dihydro-isoxazol-5-ylmethyl)-carbamoyl]-ethyl}-carbamic acid benzyl ester; (S)-2-Acetylamino-N-(3-bromo-4,5-dihydro-isoxazol-5-ylmethyl)-3-phenyl-propionamide; {(R)-1-[(3-Bromo-4,5-dihydro-isoxazol-5-ylmethyl)-carbamoyl]-2-phenyl-ethyl}-carbamic acid benzyl ester; {(S)-2-Benzylcarbamoyl-1-[(3-bromo-4,5-dihydro-isoxazol-5-ylmethyl)-carbamoyl]-ethyl}-carbamic acid benzyl ester; [(S)-1-[(3-Bromo-4,5-dihydro-isoxazol-5-ylmethyl)-carbamoyl]-2-(1H-indol-3-yl)-ethyl]-carbamic acid benzyl ester; {(S)-1-[(3-Bromo-4,5-dihydro-isoxazol-5-ylmethyl)-methyl-carbamoyl]-2-phenyl-ethyl}-carbamic acid benzyl ester; and [(S)-1-[(3-Bromo-4,5-dihydro-isoxazol-5-ylmethyl)-methyl-carbamoyl]-2-(4-hydroxy-phenyl)-ethyl]-carbamic acid benzyl ester.

8. A method of treating Celiac Sprue, the method comprising:
   orally administering to a patient an effective dose of 0.01 mg to 500 mg/kg body weight per day of the tissue transglutaminase (tTGase) inhibitor:

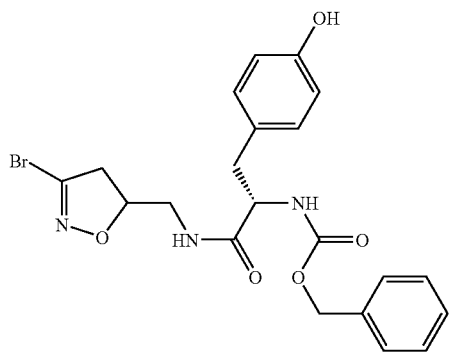

[(S)-1-[(3-Bromo-4,5-dihydro-isoxazol-5-ylmethyl)-methyl-carbamoyl]-2-(4-hydroxy-phenyl)-ethyl]-carbamic acid benzyl ester;
   wherein said tTGase inhibitor attenuates gluten toxicity in said patient.

9. The method of claim 8, wherein said tTGase inhibitor is administered with a glutenase.

10. The method according to claim 8, wherein said tTGase inhibitor is contained in a formulation that comprises an enteric coating.

* * * * *

UNITED STATES PATENT AND TRADEMARK OFFICE
CERTIFICATE OF CORRECTION

| | | |
|---|---|---|
| PATENT NO. | : 7,265,093 B2 | Page 1 of 1 |
| APPLICATION NO. | : 10/716846 | |
| DATED | : September 4, 2007 | |
| INVENTOR(S) | : Khosla et al. | |

It is certified that error appears in the above-identified patent and that said Letters Patent is hereby corrected as shown below:

Column 1:

• Please replace lines 15-17 with:

--FEDERALLY SPONSORED RESEARCH OR DEVELOPMENT
This invention was made with Government support under contract DK56339 awarded by the National Institutes of Health. The Government has certain rights in this invention.--

Signed and Sealed this
Nineteenth Day of April, 2011

David J. Kappos
*Director of the United States Patent and Trademark Office*

SEQUENCE LISTING

```
<160> NUMBER OF SEQ ID NOS: 8

<210> SEQ ID NO 1
<211> LENGTH: 10
<212> TYPE: PRT
<213> ORGANISM: Artificial Sequence
<220> FEATURE:
<223> OTHER INFORMATION: synthetic polypeptides

<400> SEQUENCE: 1

Leu Pro Tyr Pro Gln Pro Gln Leu Pro Tyr
1               5                   10

<210> SEQ ID NO 2
<211> LENGTH: 10
<212> TYPE: PRT
<213> ORGANISM: Artificial Sequence
<220> FEATURE:
<223> OTHER INFORMATION: synthetic polypeptides
<220> FEATURE:
<221> NAME/KEY: VARIANT
<222> LOCATION: (10)...(10)
<223> OTHER INFORMATION: Phenylalanine with NH2 attached

<400> SEQUENCE: 2

Leu Pro Phe Pro Gln Pro Gln Leu Pro Phe
1               5                   10

<210> SEQ ID NO 3
<211> LENGTH: 9
<212> TYPE: PRT
<213> ORGANISM: Artificial Sequence
<220> FEATURE:
<223> OTHER INFORMATION: synthetic polypeptides

<400> SEQUENCE: 3

Leu Pro Tyr Pro Gln Pro Gln Leu Pro
1               5
```

```
<210> SEQ ID NO 4
<211> LENGTH: 16
<212> TYPE: PRT
<213> ORGANISM: Artificial Sequence
<220> FEATURE:
<223> OTHER INFORMATION: synthetic polypeptides

<400> SEQUENCE: 4

Leu Pro Tyr Pro Gln Pro Gln Leu Pro Tyr Pro Gln Pro Gln Pro Phe
 1               5                  10                  15

<210> SEQ ID NO 5
<211> LENGTH: 10
<212> TYPE: PRT
<213> ORGANISM: Artificial Sequence
<220> FEATURE:
<223> OTHER INFORMATION: synthetic polypeptides

<400> SEQUENCE: 5

Pro Gln Pro Gln Leu Pro Tyr Pro Gln Pro
 1               5                  10

<210> SEQ ID NO 6
<211> LENGTH: 10
<212> TYPE: PRT
<213> ORGANISM: Artificial Sequence
<220> FEATURE:
<223> OTHER INFORMATION: synthetic polypeptides
<220> FEATURE:
<221> NAME/KEY: ACETYLATION
<222> LOCATION: (1)...(1)

<400> SEQUENCE: 6

Pro Gln Pro Gln Leu Pro Phe Pro Gln Pro
 1               5                  10

<210> SEQ ID NO 7
<211> LENGTH: 8
<212> TYPE: PRT
<213> ORGANISM: Artificial Sequence
<220> FEATURE:
<223> OTHER INFORMATION: synthetic polypeptides

<400> SEQUENCE: 7

Gln Leu Gln Pro Phe Pro Gln Pro
 1               5

<210> SEQ ID NO 8
<211> LENGTH: 15
<212> TYPE: PRT
<213> ORGANISM: Artificial Sequence
<220> FEATURE:
<223> OTHER INFORMATION: synthetic polypeptides

<400> SEQUENCE: 8

Leu Gln Leu Gln Pro Phe Pro Gln Pro Leu Pro Tyr Pro Gln Pro
 1               5                  10                  15
```